(12) United States Patent
Hirschfeld

(10) Patent No.: US 11,419,672 B2
(45) Date of Patent: Aug. 23, 2022

(54) ELECTROSURGICAL SYSTEM AND METHOD FOR OPERATING THE SAME

(71) Applicant: OLYMPUS WINTER & IBE GMBH, Hamburg (DE)

(72) Inventor: Simon Hirschfeld, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 1044 days.

(21) Appl. No.: 15/401,365

(22) Filed: Jan. 9, 2017

(65) Prior Publication Data

US 2017/0112565 A1 Apr. 27, 2017

Related U.S. Application Data

(63) Continuation of application No. PCT/EP2015/068419, filed on Aug. 11, 2015.

(30) Foreign Application Priority Data

Aug. 27, 2014 (DE) ..................... 10 2014 217 095.8

(51) Int. Cl.
*A61B 18/14* (2006.01)
*A61B 90/96* (2016.01)
(Continued)

(52) U.S. Cl.
CPC .............. *A61B 18/149* (2013.01); *A61B 1/04* (2013.01); *A61B 18/1482* (2013.01); *A61B 90/361* (2016.02); *A61B 90/90* (2016.02); *A61B 90/92* (2016.02); *A61B 90/94* (2016.02); *A61B 90/96* (2016.02); *A61B 2017/00057* (2013.01);
(Continued)

(58) Field of Classification Search
CPC ..................................................... A61B 90/96
See application file for complete search history.

(56) References Cited

U.S. PATENT DOCUMENTS 4,649,917 A * 3/1987 Karasawa ............ A61B 18/149
606/46
5,649,021 A * 7/1997 Matey ...................... G06K 9/46
348/65
(Continued)

FOREIGN PATENT DOCUMENTS

DE 10 2009 017 616 A1 5/2010
DE 10 2013 002 832 A1 9/2014
(Continued)

OTHER PUBLICATIONS

Oct. 28, 2015 International Search Report issued in International Application No. PCT/EP2015/068419.

*Primary Examiner* — Ronald Hupczey, Jr.
(74) *Attorney, Agent, or Firm* — Oliff PLC

(57) ABSTRACT

The disclosed embodiments relate to an electrosurgical system, to a method for operating an electrosurgical system, and to an electrode for an electric surgical system. An image detection system of the surgical instrument detects an image of the electrode. The corresponding image data is compared with data sets in a database, in which an identifying feature of the electrode and at least one operating parameter for the electrode are assigned to each other. After the electrode type has been identified, the corresponding operating parameters are transmitted to a controller of the surgical instrument.

10 Claims, 2 Drawing Sheets

(51) Int. Cl.

| | | |
|---|---|---|
| *A61B 90/92* | (2016.01) | |
| *A61B 90/94* | (2016.01) | |
| *A61B 90/90* | (2016.01) | |
| *A61B 90/00* | (2016.01) | |
| *A61B 1/04* | (2006.01) | |
| *A61B 17/00* | (2006.01) | |
| *A61B 18/00* | (2006.01) | |

(52) U.S. Cl.
 CPC ............ *A61B 2017/00482* (2013.01); *A61B 2018/00601* (2013.01); *A61B 2018/00607* (2013.01); *A61B 2018/00982* (2013.01); *A61B 2018/1407* (2013.01); *A61B 2018/1495* (2013.01)

(56) References Cited

U.S. PATENT DOCUMENTS

| | | | | |
|---|---|---|---|---|
| 6,074,386 A | * | 6/2000 | Goble | A61B 18/1206 606/34 |
| 6,235,020 B1 | * | 5/2001 | Cheng | A61B 18/1492 606/34 |
| 7,033,351 B2 | * | 4/2006 | Howell | A61B 18/08 606/29 |
| 7,614,554 B2 | * | 11/2009 | Mott | G16H 40/20 235/440 |
| 9,168,104 B2 | * | 10/2015 | Dein | A61B 90/96 |
| 2005/0203544 A1 | * | 9/2005 | Revie | A61B 17/1615 606/130 |
| 2008/0262654 A1 | | 10/2008 | Omori et al. | |
| 2009/0275940 A1 | * | 11/2009 | Malackowski | A61B 18/1233 606/42 |
| 2009/0317002 A1 | * | 12/2009 | Dein | A61B 50/36 382/224 |
| 2011/0111522 A1 | * | 5/2011 | Zimmerie | A61B 90/96 436/501 |
| 2012/0181331 A1 | * | 7/2012 | Beden | A61B 90/98 235/375 |
| 2013/0046299 A1 | | 2/2013 | Newkirk | |
| 2014/0288460 A1 | * | 9/2014 | Ouyang | A61B 1/0005 600/570 |

FOREIGN PATENT DOCUMENTS

| | | |
|---|---|---|
| EP | 2 008 598 A1 | 12/2008 |
| EP | 2 110 698 A2 | 10/2009 |
| EP | 2 329 783 A1 | 6/2011 |
| EP | 2 641 552 A2 | 9/2013 |
| JP | 2001-112774 A | 4/2001 |
| JP | 2009-201618 A | 9/2009 |
| WO | 2013/186534 A1 | 12/2013 |

* cited by examiner

ELECTROSURGICAL SYSTEM AND METHOD FOR OPERATING THE SAME

BACKGROUND

The disclosed embodiments relate to an electrosurgical system comprising a surgical instrument with an imaging system and a shaft, wherein an electrode holder is arranged on a distal end of the shaft, and wherein the imaging system is configured to capture a surgical field that extends distally from the distal end of the shaft. The disclosed embodiments further relate to a method for operating such an electrosurgical system. Finally, the disclosed embodiments relate to an electrode for an electrosurgical system.

In high-frequency surgery (also termed HF surgery), a high-frequency alternating current is conducted through a tissue to be operated on in order to intentionally damage or cut it. The major advantage of this surgical technique in comparison to using a conventional scalpel is that blood is stanched by the closure of the relevant vessels at the same time as the incision. In high-frequency surgery, an electrode that is used instead of a scalpel is mounted on a surgical instrument such as a resectoscope. When operating the electrode, it is important to operate it using the provided operating parameters.

Setting the correct operating parameters is made easier for the surgeon in that the surgical instrument is capable of independently identifying the mounted electrode. For this purpose, an integrated circuit (IC) is located in the plug of the electrode. It is however technically involved and expensive to integrate such ICs in the electrode. Since such electrodes are sometimes disposable articles for hygienic reasons, the cost of the electrodes contributes directly to the operating costs of the electrosurgical system.

SUMMARY

An object of the disclosed embodiments is to present an electrosurgical system, a method for operating an electrosurgical system, as well as an electrode for an electrosurgical system as well as its use, wherein the operating costs of the electrosurgical system and the fabrication effort in producing the electrosurgical system is minimal, The object is achieved by an electrosurgical system comprising a surgical instrument with an imaging system and a shaft, wherein an electrode holder is arranged on a distal end of the shaft, and wherein the imaging system is configured to capture a surgical field that extends distally from the distal end of the shaft, the electrosurgical system further comprising:
  an electrode that is connectible to the electrode holder for performing a surgical procedure, wherein the electrode comprises an optically detectable external identifying feature,
  a data processing unit having a database that comprises a plurality of data sets in which information relating to at least one identifying feature of an electrode type and at least one operating parameter provided for operating this electrode type are assigned to each other,
  wherein
  the imaging system is configured to capture an image of the electrode and to transfer the image data of the captured image to the data processing unit, and
  the data processing unit is configured
    to analyze the received image data with regard to an identifying feature in the image data,
    to compare a found identifying feature with the data sets in the database, and
    to identify a type of electrode and to transmit the associated at least one operating parameter to a controller of the surgical instrument.

The invention is based on the consideration that the operating costs of an electrosurgical system are lowered when the existing imaging system of the surgical instrument is applied to recognize a type of the employed electrode.

Furthermore, an external identifying feature of the electrode is applied to identify its type. Advantageously, an electronic identification of the electrode such as an IC in the plug of the electrode is dispensed with. These measures lower the unit costs of the electrodes and accordingly also the operating costs of the electrosurgical system.

In particular, after the operating parameters are transmitted to a controller of the surgical instrument, the electrosurgical system is also operated with these operating parameters.

Moreover, according to an advantageous embodiment, the identifying feature is at least a part of an external shape of the electrode, and/or a machine-readable code on an external surface of the electrode.

A part of the external shape is for example dimensions and/or relative sizes of individual components of the electrode. Furthermore, edges, chamfers, arrangements of connecting or joint seams, etc. are suitable identifying features. For example, a barcode, or a QR code, or likewise a color code can be used as the machine-readable code. Color dots that are applied by machine are preferably used as the color code. A barcode or a QR code is in particular applied to the electrode using a laser marking device. Advantageously, the electrode can be identified with little effort which lowers its production costs. According to another exemplary embodiment, the electrode comprises:
  an active region that is in contact with tissue to be treated while performing the surgical procedure, and
  a connecting region provided for electrically contacting the electrode having at least one electrical connecting contact,
  wherein the at least one electrical connecting contact and the active region are connected to each other by an electrical supply line visible from the outside, and
  wherein a color and/or a color code of the electrical supply line, in particular an electrical insulation of the supply line, are the identifying feature.

Depending on the operating parameters of the employed electrode such as the current and/or voltage provided for operation, electrical supply lines with different dimensions are used for contacting the connecting contacts to the active region. The electrical supply lines are typically marked with different colors or color codes so that they can be identified while producing the electrode. This information that is already integrated by the manufacturer when producing the electrode in the form of the employed electrical supply lines is advantageously useful for determining the type of electrode at a later time. It is particularly advantageous when no additional steps have to be integrated in the production process for identifying the electrode.

According to another advantageous embodiment, the at least one operating parameter comprises an operating voltage, and/or an operating current, and/or an operating frequency, and/or a maximum operating voltage, and/or a maximum operating current, and/or a maximum operating frequency provided for operating the electrode.

In particular, the surgical instrument is an endoscope. Moreover, the surgical instrument is in particular a resectoscope, and the electrode is a resection electrode.

Both monopolar and bipolar electrodes are provided as the electrode.

The object according to the disclosed embodiments is furthermore achieved by a method for operating an electrosurgical system according to one or more of the cited embodiments, wherein the method comprises the following method steps:

the imaging system captures an image of the electrode and transfers the image data of the captured image to the data processing unit, the data processing unit analyzes the received data with regard to an identifying feature in the image data, a found identifying feature is compared with the data sets in the database, and a type of electrode is identified, and the associated at least one operating parameter is transmitted to a controller of the surgical instrument.

In particular, the electrosurgical system is also operated with the parameters transferred by the data processing unit to the controller.

According to one embodiment, the method is developed in that the data processing unit analyzes in the image data at least a part of an external shape of the electrode, and/or a machine-readable code on the external surface of the electrode, and/or a color, and/or a color code of an electrical supply line as the identifying feature in the image data.

Furthermore, an operating voltage, and/or an operating current, and/or an operating frequency, and/or maximum operating voltage, and/or maximum operating current, and/or maximum operating frequency provided for operating the electrode is transmitted by the data processing unit to the controller of the surgical instrument as the operating parameter.

The same or similar advantages apply to the method for operating the electrosurgical system that were mentioned above with reference to the electrosurgical system itself, and they will therefore not be repeated at this juncture.

The object according to the disclosed embodiments is furthermore achieved by an electrode for an electrosurgical system, or an electrosurgical system according to one or more embodiments, wherein the electrode comprises a machine-readable code on an external surface of the electrode as an optically-detectable external identifying feature.

A barcode and/or a QR code are for example suitable as the machine-readable code that is/are applied in particular to the surface of the electrode using a laser engraving method. Furthermore, a mechanically-applied color code, in particular consisting of color dots, is suitable as the identifying feature.

Moreover, a particular external shape of the electrode in particular such as an external dimension, relative sizes, a length of a specific component, an edge and/or chamfer are suitable as the external identifying feature of the electrode. One or more of these features are advantageously used as the identifying feature of the electrode.

Finally, the object is achieved by using an electrode, in particular an electrode according to one of the cited embodiments, comprising an optically detectable external identifying feature in an electrosurgical system according to one of the embodiments.

The same or similar advantages apply to the electrode and its use that were mentioned above with reference to the electrosurgical system or the method; repetitions will therefore be dispensed with.

Further features of the disclosed embodiments will become apparent from the description herein together with the claims and the included drawings. Embodiments according to the invention can fulfill individual characteristics or a combination of several characteristics,

BRIEF DESCRIPTION OF THE DRAWINGS

The disclosed embodiments will be described below using exemplary embodiments with reference to the drawings without being limited thereto, and for any details which are not explained further in the text, express reference is made to the drawings. The figures show the following.

In the drawings, the same or similar types of elements and/or parts are provided with the same reference numbers so that a re-introduction is omitted.

DETAILED DESCRIPTION OF EMBODIMENTS

Figure 1:
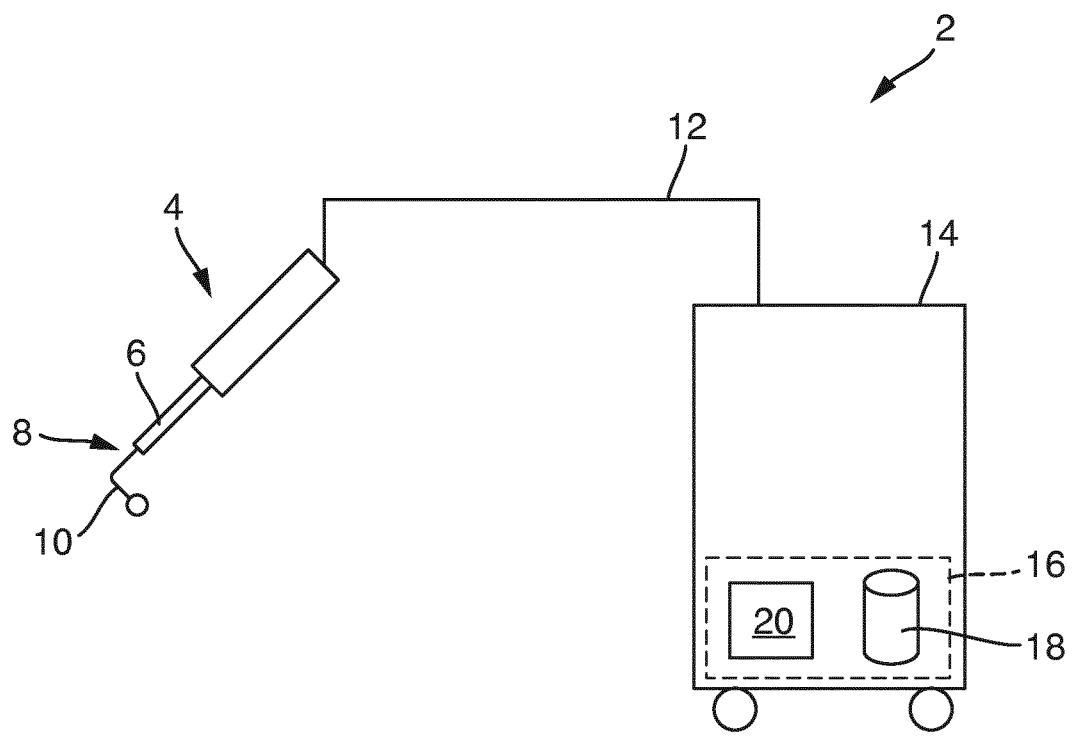
FIG. 1 shows a schematic representation of an electrosurgical system.

FIG. 1 shows a schematic, simplified view of an electrosurgical system 2 comprising a surgical instrument 4 with an imaging system (not shown) and a shaft 6. An electrode holder is arranged at a distal end 8 of the shaft 6. This serves to accommodate an electrode 10 for performing a surgical procedure.

A resectoscope is shown as an example of a surgical instrument 4 in FIG. 1. Correspondingly, the electrode 10 is a resection electrode, i.e., a loop.

The surgical instrument 4 is connected by a supply line 12 to a control unit 14. The supply line 12 serves to supply electricity to the surgical instrument 4 as well as to transmit data between the control unit 14 and surgical instrument 4.

In addition to other generally known units that are not shown, the control unit 14 comprises a data processing unit 16 such as a computer having a database 18. There is a plurality of data sets in the database 18 that for example are saved on a non-volatile memory. Each of these data sets contains information on at least one identifying feature of an electrode type, and at least one operating parameter for operating this electrode type. These two pieces of information are assigned to each other.

The imaging system of the surgical instrument 4 is configured to capture an image of the electrode 10 and to transfer the associated image data of the captured image to the data processing unit 16. Data is transmitted, for example, by the supply line 12. This can also be performed in another way, such as wirelessly. The data processing unit 16 is configured to analyze the received image data with regard to an identifying feature in the image data. If the data processing unit 16 finds an identifying feature in the image data, it is compared with the data sets in the database 18. More precisely, there is a comparison with the information on different identifying features of different electrode types in the data sets. The data processing unit 16 accordingly identifies the type of electrode 10 whose image was captured. It retrieves the associated operating parameters for this type of electrode from the associated data set in the database 18. These operating parameters are transmitted to a controller 20 of the surgical instrument 4. Finally, the surgical instrument 4 is operated with these operating parameters. For example, an appropriate current and appropriate voltage is set.

FIG. 1 shows the controller 20 of the surgical instrument 4 as a part of the data processing unit 16 only as an example.

In the described electrosurgical system 2, the controller 20 is therefore automatically set to the correct operating parameters for the electrode 10. In this context, the empirical set is used when the electrode 10 is, at least briefly, in the field of vision of the imaging system of the surgical instrument 4 before the electrode 10 is connected to the electrode holder at the distal end 8 of the shaft 6. The user is therefore able to capture and evaluate an image of the electrode 10 without additional steps.

If the image captured in this manner is insufficient, for example, the identifying feature of the electrode 10 is not visible; the control unit 14 is optionally configured to output information to the user of the surgical instrument 4 to move the electrode 10 into the field of vision of the imaging system. For example, a visual or acoustic request is output.

Figure 2:
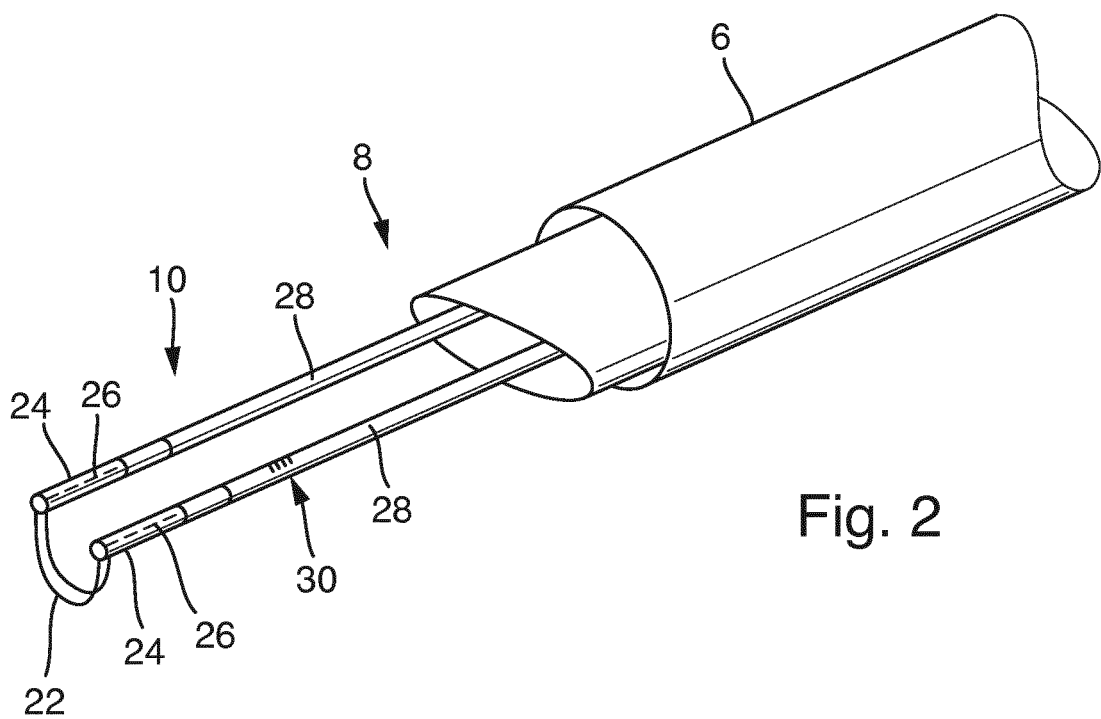
FIG. 2 shows a schematic perspective view of a region of a distal shaft end of a resectoscope with a connected electrode.

FIG. 2 shows a simplified, schematic perspective view of a distal end region of the shaft 6 of the surgical instrument 4. The electrode 10 comprises an active region 22 that is designed in the shape of a loop. A bipolar electrode 10 is shown as an example. However, the electrosurgical system 2 is also set up for monopolar electrodes. While a surgical procedure is being performed, the active region 22 is in contact with the tissue to be treated.

Adjacent to the active region 22 is a transitional region that is formed from a pair of transparent tubes 24 and electrical supply lines 26 running therein. In the proximal direction, a connecting region 28 for the electrode 10 is adjacent to this transitional region. At a proximal end of the connecting region 28 that is not visible in FIG. 2, there is an electrical connecting contact, or plug. This is inserted into the electrode holder of the shaft 6 of the surgical instrument 4 to establish an electrical contact.

The electrical supply lines 26 are visible from the outside through the transparent tubes 24. Depending on the type of electrode 10, differently colored electrical supply lines 26 are used to produce it. Likewise, the electrical supply lines 26 are encoded with differently colored codes selected for this purpose.

It is therefore possible to identify the electrode 10 according to its type by the color and/or color code of the electrical supply lines 26. This color or color code is accordingly assigned the role of an identifying feature.

Furthermore, an external shape of the electrode 10 or a machine-readable code 30 on an external surface of the electrode 10 is used as the identifying feature. The machine-readable code 30 is for example a barcode and/or a QR code. This is in particular applied to the electrode 10 in a laser engraving method.

Figure 3:
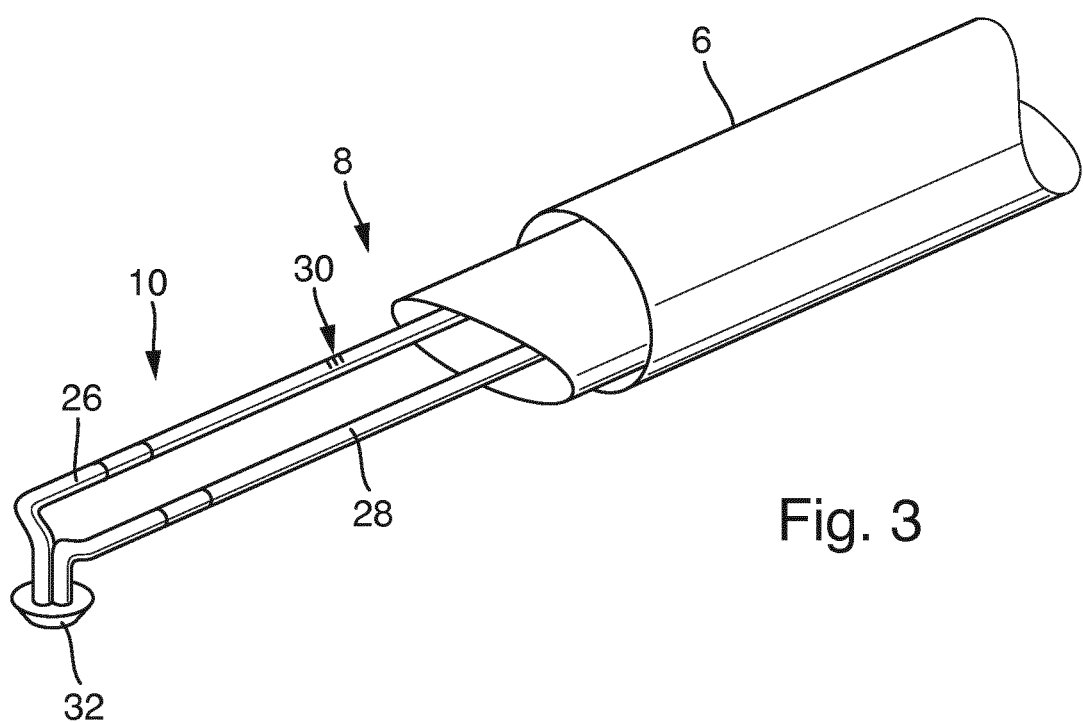
FIG. 3 shows another schematic perspective view of a distant distal shaft end of another resectoscope with a connected additional electrode.

In another schematically simplified perspective view, FIG. 3 shows a part of the shaft 6 of the surgical instrument 4 in the region of its distal end 8. The electrode 10 that is picked up by the electrode holder at the distal end 8 of the shaft 6 is not an electroloop as shown in FIG. 2, but rather an electrode 10 with a button electrode 32. This is connected by two electrical supply lines 26 to the connecting region 28 of the electrode 10. In addition to a machine-readable code 30 and the shape of the electrode 10, a color and/or color code of the insulation of the supply lines 26 are provided as an identifying feature of the electrode 10.

After the type of the electrode 10 has been identified, for example an operating voltage and/or operating current, and/or an operating frequency provided for operating the electrode 10 is fed to the controller 20 as an operating parameter. Likewise, the corresponding maximum values of the operating voltage, the operating current, and/or a maximum operating frequency are transmitted as operating parameters.

The disclosed embodiments can be realized by the individual features disclosed herein, or a combination of several features. Features that are designated with "in particular" or "preferably" are optional features.

What is claimed is:

1. An electrosurgical system comprising:
   a surgical instrument comprising:
      a shaft;
      an imaging system configured to capture a surgical field that extends distally from a distal end of the shaft; and
      an electrode holder arranged on the distal end of the shaft;
   a control unit comprising:
      a data processing unit having comprising:
         a controller; and
         a database that comprises a plurality of data sets in which information relating to (i) at least one optically detectable external electrode identifying feature and (ii) at least one associated electrode operating parameter, are assigned to each other; and
   an electrode that is connectible to the electrode holder for performing a surgical procedure, the electrode comprising one of the at least one electrode identifying features,
   wherein:
   the at least one optically detectable external electrode identifying feature comprises an external shape of the electrode selected from the group consisting of an external dimension of a part of the electrode, relative sizes of individual components of the electrode, a length of a specific component of the electrode, and the presence and/or arrangement of edges, chamfers, and connecting or joint seams,
   the at least one electrode operating parameter comprises an operating frequency, and/or a maximum operating voltage, and/or a maximum operating current, and/or a maximum operating frequency provided for operating the electrode,
   the imaging system is configured to:
      capture a surgical field that extends distally from the distal end of the shaft, and
      capture an image of the electrode when the electrode is in a field of vision of the imaging system and detached from the electrode holder, and transfer image data of the captured image to the data processing unit,
   the data processing unit is configured to:
      analyze the transferred image data with regard to the electrode identifying feature of the electrode in the image data,
      compare the found electrode identifying feature with the data sets in the database, and
      identify the electrode and transmit the associated electrode operating parameter to the controller, and
   the control unit is configured to output information to a user of the surgical instrument to move the electrode into the field of vision of the imaging system if the electrode identifying feature is not found in the captured image.

2. The electrosurgical system according to claim 1, wherein the electrode comprises:
   an active region configured to contact tissue to be treated while performing the surgical procedure; and
   a connecting region having at least one electrical connecting contact configured to contact the electrode with the electrode holder.

3. The electrosurgical system according to claim 1, wherein the surgical instrument is an endoscope.

4. The electrosurgical system according to claim 3, wherein the endoscope is a resectoscope, and the electrode is a resection electrode.

5. The electrosurgical system according to claim 1, wherein:
   the electrode identifying feature of the electrode is configured to identify the type of electrode, and
   the data processing unit is configured to identify the type of electrode and transmit the associated electrode operating parameter to the controller.

6. The electrosurgical system according to claim 1, wherein the at least one electrode operating parameter comprises an operating frequency and/or a maximum operating frequency provided for operating the electrode.

7. The electrosurgical system according to claim 1, wherein the at least one optically detectable external electrode identifying feature further comprises a barcode on an external surface of the electrode.

8. The electrosurgical system according to claim 1, wherein the at least one optically detectable external electrode identifying feature further comprises a QR code on an external surface of the electrode.

9. A method of operating the electrosurgical system according to claim 1, the method comprising:
   capturing the image of the electrode with the imaging system and transferring the image data of the captured image to the data processing unit;
   analyzing the transferred image data with regard to the electrode identifying feature of the electrode in the image data;
   comparing the found electrode identifying feature with the data sets in the database; and
   identifying the electrode, and transmitting the associated electrode operating parameter to the controller.

10. An electrosurgical system comprising:
    a surgical instrument comprising:
       a shaft;
       an imaging system configured to capture a surgical field that extends distally from a distal end of the shaft; and
       an electrode holder arranged on the distal end of the shaft;
    a control unit comprising:
       a data processing unit comprising:
          a controller; and
          a database that comprises a plurality of data sets in which information relating to (i) at least one optically detectable external electrode identifying feature and (ii) at least one associated electrode operating parameter, are assigned to each other; and
    an electrode that is connectible to the electrode holder for performing a surgical procedure, the electrode comprising one of the at least one electrode identifying features,
    wherein:
    the at least one optically detectable external electrode identifying feature consists of an external shape of the electrode, the at least one electrode operating parameter comprises an operating frequency, and/or a maximum operating voltage, and/or a maximum operating current, and/or a maximum operating frequency provided for operating the electrode,
    the imaging system is configured to:
       capture a surgical field that extends distally from the distal end of the shaft, and
       capture an image of the electrode when the electrode is in a field of vision of the imaging system and detached from the electrode holder, and transfer image data of the captured image to the data processing unit,
    the data processing unit is configured to:
       analyze the transferred image data with regard to the electrode identifying feature of the electrode in the image data,
       compare the found electrode identifying feature with the data sets in the database, and
       identify the electrode and transmit the associated electrode operating parameter to the controller, and
    the control unit is configured to output information to a user of the surgical instrument to move the electrode into the field of vision of the imaging system if the electrode identifying feature is not found in the captured image.

* * * * *